United States Patent [19]

Schichman et al.

[11] Patent Number: 5,452,395
[45] Date of Patent: Sep. 19, 1995

[54] LIQUID LIGHT GUIDE FOR ENDOSCOPIC INSTRUMENTATION

[75] Inventors: Daniel Schichman, Trumbull; Oleg Shikhman, Bridgeport, both of Conn.

[73] Assignee: United States Surgical Corporation, Norwalk, Conn.

[21] Appl. No.: 134,365

[22] Filed: Oct. 8, 1993

[51] Int. Cl.$^6$ ............................................. G02B 6/20
[52] U.S. Cl. ................... 385/125; 385/124; 385/117; 362/32; 600/182; 600/140
[58] Field of Search ............. 385/125, 122, 123, 124, 385/126, 127, 117; 128/6, 4; 362/32

[56] References Cited

U.S. PATENT DOCUMENTS

| | | | |
|---|---|---|---|
| 3,089,484 | 5/1963 | Hett | 128/6 |
| 3,641,332 | 2/1972 | Reick et al. | 362/32 |
| 3,740,113 | 6/1973 | Cass | 385/125 |
| 3,770,350 | 11/1973 | Stone et al. | 356/75 |
| 3,814,497 | 6/1974 | Stone | 385/125 |
| 3,920,980 | 11/1975 | Nath | 362/32 |
| 3,995,934 | 12/1976 | Nath | 385/125 |
| 4,009,382 | 2/1977 | Nath | 362/32 |
| 4,045,119 | 8/1977 | Eastgate | 385/125 |
| 4,286,839 | 9/1981 | Ilzig et al. | 385/125 |
| 4,465,621 | 8/1984 | Sacher | 252/582 |
| 4,471,474 | 9/1984 | Fields | 367/149 |
| 4,491,533 | 1/1985 | Sacher et al. | 252/301 |
| 4,526,711 | 7/1985 | Sacher et al. | 252/582 |
| 4,747,662 | 5/1988 | Fitz | 385/125 |
| 4,801,187 | 1/1989 | Elbert et al. | 385/31 |
| 4,805,598 | 2/1989 | Ueda | 128/6 |
| 4,901,922 | 2/1990 | Kessener et al. | 239/12 |
| 4,907,133 | 3/1990 | Nath | 362/32 |
| 4,927,231 | 5/1990 | Levatter | 385/31 |
| 4,957,347 | 9/1990 | Zarian | 350/96.32 |
| 5,052,778 | 10/1991 | Jamshid | 385/125 |
| 5,067,831 | 11/1991 | Robbins et al. | 385/123 |
| 5,143,435 | 9/1992 | Kikuchi | 362/32 |
| 5,149,467 | 9/1992 | Zarian | 264/1.5 |
| 5,165,773 | 11/1992 | Nath | 362/32 |
| 5,221,387 | 6/1993 | Robbins et al. | 156/85 |
| 5,257,329 | 10/1993 | Blyler, Jr. et al. | 385/11 |
| 5,267,341 | 11/1993 | Shearin | 385/125 |
| 5,333,227 | 7/1994 | Ishiharada et al. | 385/100 |

FOREIGN PATENT DOCUMENTS 48867 5/1974 Australia .
(List continued on next page.)

OTHER PUBLICATIONS

Copy of Search Report from Corresponding European Patent Application no. 94115362.9.
Liquid Optical Fibers, G. W. Taylor, vol. 11, No. 4, Apr. 1972 (pp. 786–790).
English language Abstract for German Publication No. 4014363, 1990 No Month.

*Primary Examiner*—Frank Gonzalez
*Assistant Examiner*—Phan T. H. Palmer

[57] ABSTRACT

Generally stated, the present invention is directed to a liquid light guide for surgical instrumentation, which includes a flexible elongated tube having first and second end portions, first and second light transmissive members disposed at respective first and second end portions of the elongated tube to substantially seal an interior portion of the elongated tube and a light transmissive medium filing the interior portion of the elongated tube. The preferred light transmissive medium comprises a heavy mineral oil having a specific gravity greater than or equal to about 0.86. Preferred light transmissive members are drawn glass rods having polished ends and an index of refraction substantially equal to the transmissive medium. The liquid light guide of the present invention is capable of providing nearly 100% light transmission over the entire visible spectral range while substantially reducing undesired transmission of infrared and ultraviolet radiation. The light guide is contemplated to be used with an endoscope and is cost-effective to manufacture such that the light guide may be disposed of after a single use. Methods of making and using the disposable light guide also are disclosed.

38 Claims, 6 Drawing Sheets

FOREIGN PATENT DOCUMENTS

| | | |
|---|---|---|
| 0246552 | of 0000 | European Pat. Off. . |
| 0105706 | 8/1987 | European Pat. Off. . |
| 2689649 | of 0000 | France . |
| 2352670 | 10/1973 | Germany . |
| 2406424 | 2/1974 | Germany . |
| 2424620 | 5/1974 | Germany . |
| 2429859 | 6/1974 | Germany . |
| 2433218 | 7/1974 | Germany . |
| 2719504 | 5/1977 | Germany . |
| 3523243 | 6/1985 | Germany . |
| 3529488 | 8/1985 | Germany . |
| 3626629 | 8/1986 | Germany . |
| 3634651 | 10/1986 | Germany . |
| 3644839 | 12/1986 | Germany . |
| 3704871 | 2/1987 | Germany . |
| 3704872 | 2/1987 | Germany . |
| 3812473 | 4/1988 | Germany . |
| 613284 | 4/1977 | Switzerland . |
| 1450608 | 9/1976 | United Kingdom . |
| 1502445 | 3/1978 | United Kingdom . |
| 2248312 | 4/1992 | United Kingdom . |

LIQUID LIGHT GUIDE FOR ENDOSCOPIC INSTRUMENTATION

BACKGROUND OF THE INVENTION

1. Field of the Invention

The present invention relates generally to light guides for transferring illuminating light from a light source to surgical instrumentation, and, more particularly, to a flexible liquid light guide for transmitting light in the visible spectral range to an endoscope.

2. Description of the Prior Art

In endoscopic surgical procedures, illuminating light is typically transmitted from an external light source to an endoscope where the light is then transmitted via an illuminating system incorporated within the endoscope to the body cavity to be viewed. A conventional light cable for providing the endoscope with illumination is a fiber optic light bundle having a plurality of optical fibers of glass or optical plastic. The fiber optic bundle is connected at one end to the light source and at the other end to an inlet port of the endoscope. This system is typically referred to as a fiber optic light guide.

A significant drawback of fiber optic light guides concerns their degradation when used over a period of time. Such degradation is due in part to the repetitive flexing the light guide undergoes when the bundle is initially connected to the light source and the endoscope, and during maneuvering about the operative site in the course of the surgical procedure. Since fiber optic light guides are relatively expensive and are intended to be reused, the light guides are typically employed in many surgical procedures over a substantial period of time. Consequently, the light transferring quality of the fiber optic light guide tends to gradually degrade to a point where the level of light emitted by the fiber optic bundle is substantially less than the light initially received from the light source.

One attempted solution to this problem has been to substitute liquids for fiber optic bundles. Examples of such liquid light guides are described in U.S. Pat. Nos. 3,740,113; 3,920,980; 3,995,934; 4,045,119; 4,907,133 and 5,165,773. However, these liquid light guides are subject to their own drawbacks and limitations. In particular, the liquids described and suggested in these patents provide an inferior degree of visible light transmission when compared with convention fiber optic light guides. In addition, many of the liquids described are not biocompatible and are not favored for use in a surgical apparatus. Further, the construction of such known light guides entails significant expense thereby precluding disposal of the light guides after a single use. Consequently, as in conventional fiber optic light guides, these liquid light guides must also be sterilized after each application, thus adding additional expense to the user.

The present invention is directed to a low cost liquid light guide for efficiently supplying an endoscope with illuminating light particularly in the visible spectral range and which may be disposed of after a single use.

SUMMARY OF THE INVENTION

Generally stated, the present invention is directed to a liquid light guide for surgical instrumentation, which comprises a flexible elongated tube having first and second end portions, first and second light transmissive members disposed at respective first and second end portions of the elongated tube to substantially seal an interior portion of the elongated tube and an efficient light transmissive medium filling the interior portion of the elongated tube. The preferred light transmissive medium comprises a heavy mineral oil having a specific gravity greater than or equal to about 0.86 and preferably between about 0.86 and 0.905.

The liquid light guide of the present invention is capable of providing very high light transmission over the visible spectral range while reducing undesired transmission of infrared and ultraviolet radiation. The light guide is contemplated to be used with an endoscope and is cost-effective to manufacture such that the light guide may be disposed of after a single use. It is further envisioned that the light guide could be monolithically formed with a disposable endoscope and be disposable therewith as a single unit.

BRIEF DESCRIPTION OF THE DRAWINGS

Preferred embodiments of the present invention are described hereinbelow with reference to the drawings wherein.

DETAILED DESCRIPTION OF THE PREFERRED EMBODIMENT

Figure 1:
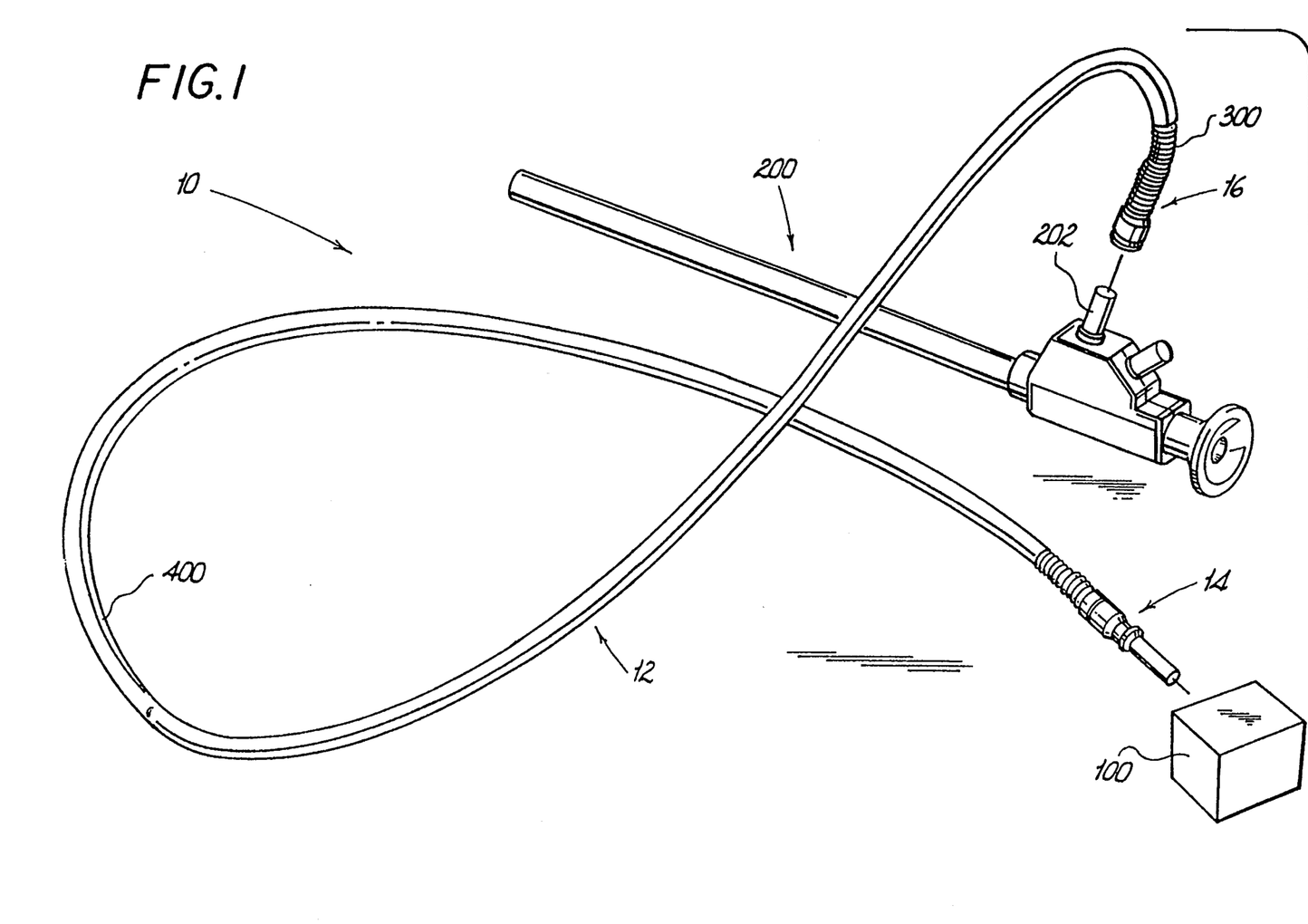
FIG. 1 is perspective view of a liquid light guide constructed in accordance with the principles of the present invention along with a conventional endoscope and light source.

Referring now to the drawings in detail in which like reference numerals identify similar or identical elements throughout the several views, FIG. 1 illustrates in perspective view a novel liquid light guide constructed in accordance with the principles of the present invention. Light guide 10 includes flexible elongated tube 12 having an illuminator connector 14 at one end portion which is configured for connection to light source 100. An endoscope connector 16 is configured for connection to endoscope 200 at illuminating inlet port 202.

Figure 2:
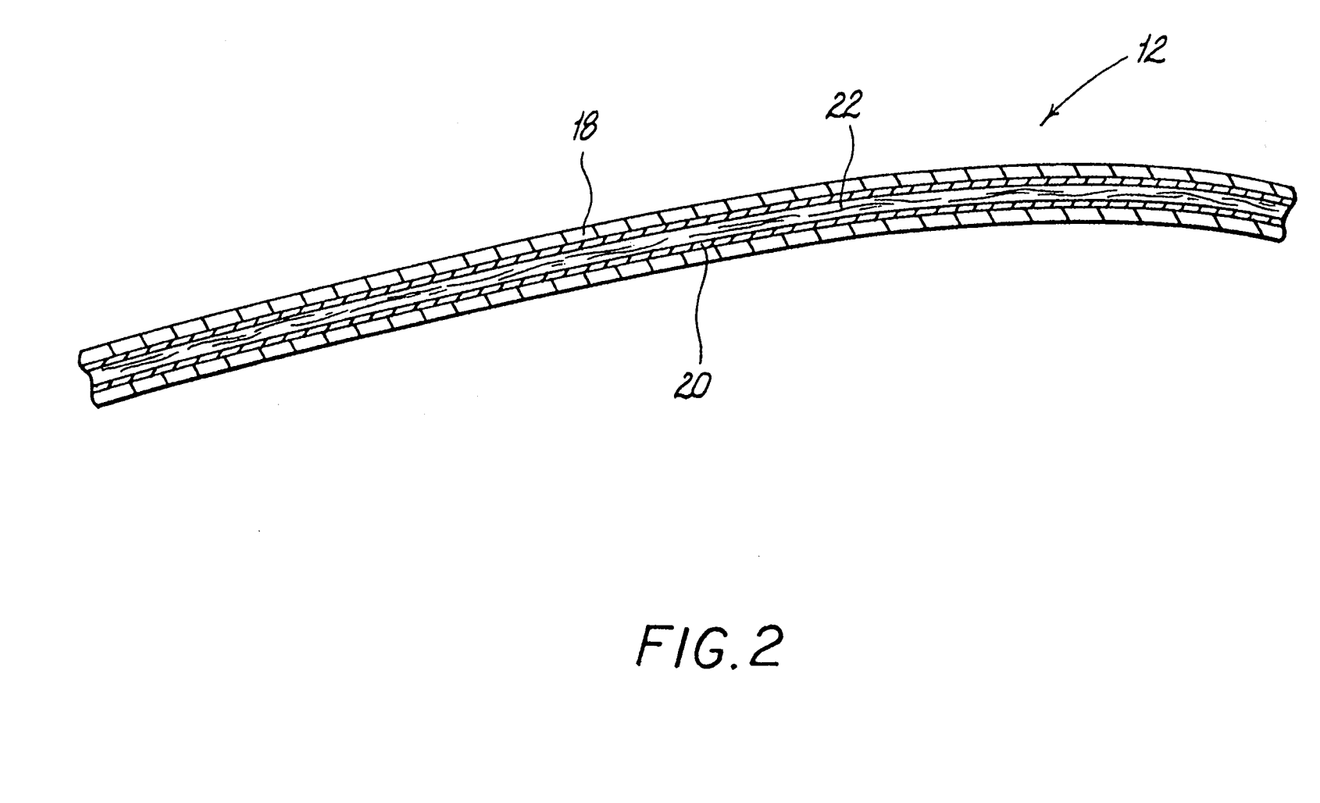
FIG. 2 is a side cross-sectional view of a portion of the flexible elongated tube of the light guide of FIG. 1 illustrating the outer sheath and inner lining.

Referring now to FIG. 2, in conjunction with FIG. 1, flexible elongated tube 12 includes an outer sheath 18 which is fabricated from a polymeric material such as polyethylene, polyvinylchloride (PVC), polytetrafluoroethylenehexafluoropropylene, perfluoralkoxy resin (PFA), a copolymer of tetrafluoroethylene and hexafluoropropylene, polytetrafluoroethylene (PTFE) and the like. Elongated tube 12 includes an inner lining 20 which extends along the length of outer sheath 18. Inner lining 20 is preferably fabricated from fluorinated ethylene polymer (FEP) although other suitable plastic materials such as the materials mentioned above may be to used to achieve a desired numerical aperture by controlling the refractive index difference between the liner and the transmissive fluid.

Outer sheath 18 and inner lining 20 may be coextruded during manufacture. Such coextruded tubing is available under the tradename PURE-LINE-1 from FURON, Inc. (New Jersey). In this embodiment, the inner diameter of outer sheath 18 is about 4.77 mm while the thickness of inner lining 20 is about 0.25 mm.

Elongated tube 12 is filled with a light transmitting medium or fluid 22 for transferring the light generated by light source 100 to illuminator inlet port 202 of endoscope 200. The preferred fluid 22 is a pharmaceutical grade heavy mineral oil having a specific gravity equal to or greater than about 0.86 and preferably within the range of between about 0.86 and 0.905. Such mineral oils when used in the configurations set forth in detail below are capable of providing very high light transmission over the visible spectral range while reducing transmission of infrared and ultraviolet radiation. This feature is particularly useful in minimizing undesirable heat transfer from light source 100 to endoscope 200.

Suitable mineral oils which are particularly effective when incorporated-in light guide 10 include Sigma #400-5 Heavy white mineral oil and Aldrich 33076-0 heavy white mineral oil. Outer sheath 18 provides added rigidity to help prevent kinking which can result in undesirable light leakage. Of course, it is contemplated that the liner could be used without an outer sheath provided sufficient structural rigidity to resist kinking is provided in some other manner.

A heavy mineral oil with a specific gravity equal to or greater than 0.86 is advantageous as a light transmitting medium in that it is essentially non-toxic, does not conduct heat well even during sustained periods of use and, as mentioned aforehand, is capable of providing very high light transmission over the entire visible spectral range.

Preferably, the mineral oil is degassed to minimize the potential of formation of gas bubbles particularly oxygen gas bubbles, during use of light guide 10. Degassing of the mineral oil is carried out prior to filling the light guide. The degassing procedure involves filling a container approximately half way with the preferred mineral oil, placing a stir bar in the oil and sealing the container with a connecting hose adapter. The container is then placed on top of a stir plate. A vacuum hose is connected to the container so that the oil is under vacuum during stirring. This procedure is continued until no more bubbles are seen.

A suitable degassing period for approximately one liter of mineral oil is about one hour with moderate stirring under vacuum (nominal 1 Torr).

The preferred mineral oil has an index of refraction of about 1.48 as compared to the index of refraction of the FEP inner lining 20 which is about 1.33. This difference in the indices of refraction of lining 20 and the mineral oil provides a relatively high numerical aperature of about 0.63, thereby optimizing performance of the light guide 10 and ensuring high levels of illumination transfer to endoscope 200. In the event a monolithic tubing is used, i.e., without a separate outer sheath, the index difference between the tubing and liquid should be such as to maintain high transmission efficiency.

Figure 4:
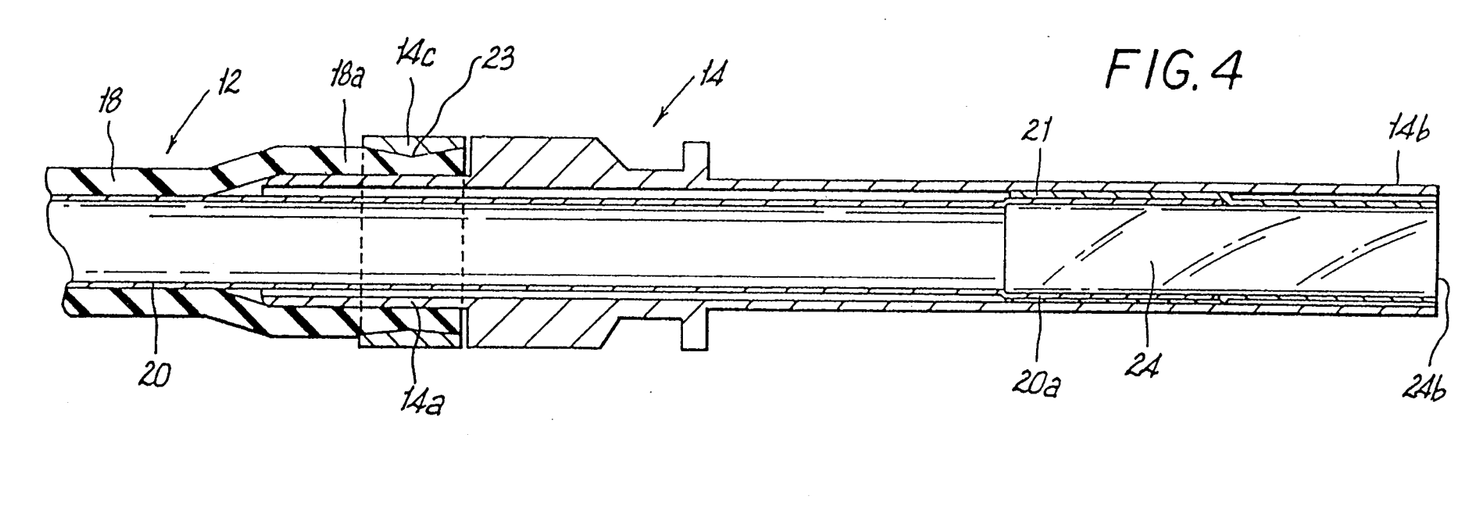
FIG. 4 is an enlarged cross-sectional view of the light source connector of FIG. 3 with a light transmissive end plug positioned therein and illustrating a preferred method for attaching the light source connector and the end plug to the flexible tube of the light guide.
Figure 6:
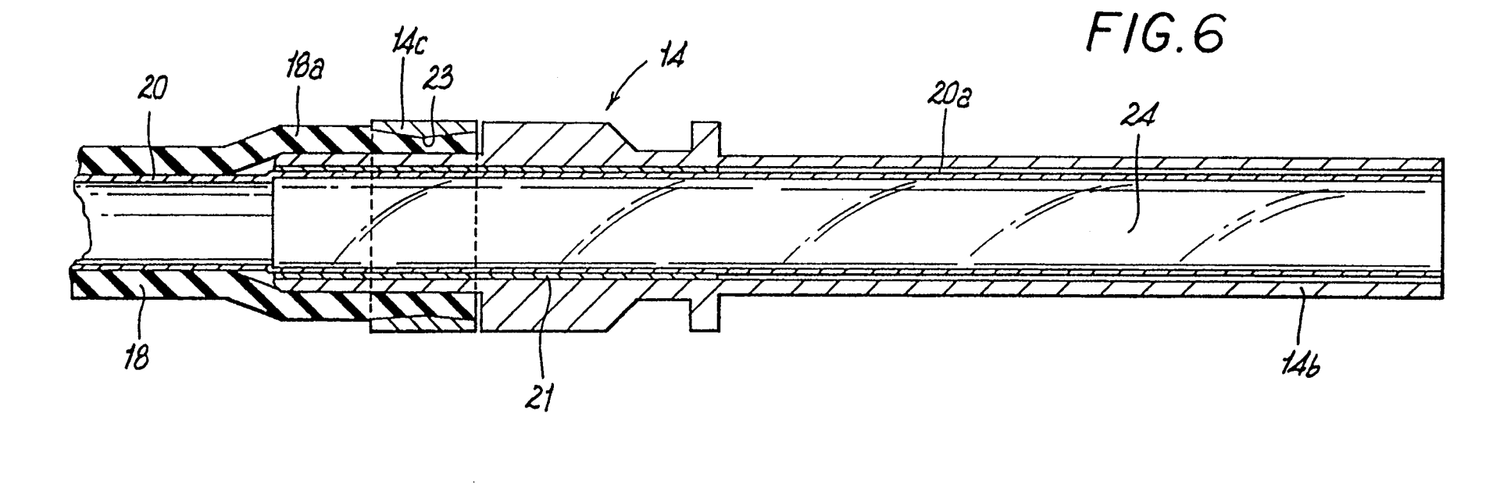
FIG. 6 is an enlarged cross-sectional view similar to FIG. 5 illustrating another alternative method for attaching the light source connector member and the elongated end plug to the flexible tube of the light guide.

Elongated tube 12 is sealed at its first or light entry end portion by transparent light transmissive plug 24 and at its second or light exit end portion by transparent light transmissive plug 26. FIG. 4 illustrates the positioning of transparent plug 24 in illuminator connector 14 while FIG. 6 illustrates the positioning of transparent plug 26 in endoscope connector 16. The preferred method for securing plugs 24, 26 to elongated tube 12 and their respective connectors 14, 16 will be discussed in greater detail below.

Transparent plugs 24, 26 are generally cylindrically shaped glass rods and are preferably fabricated from a material having an index of refraction similar to that of the light transmissive medium 22. In a preferred embodiment, transparent plugs 24, 26 are each fabricated from optical glass having an index of refraction of about 1.48 to closely match the index of refraction of the mineral oil. Suitable glass materials for transparent plugs 24, 26 include quartz, quartz glass, Pyrex TM, or any other material transparent to radiation. It is contemplated that inexpensive plastic plugs, such as polycarbonate plugs, may be used, but glass is preferred for its resistance to heat. The end faces of transparent plugs 24, 26 are polished and, if desired, may be coated with an anti-reflection coating.

In the most preferred embodiment, transparent plugs 24, 26 are glass rods formed by heat drawing techniques. Such heat drawn glass rods are considerably less expensive to manufacture than non-drawn glass rods and do not require the polishing of their peripheral surfaces to maintain optical effectiveness. The end faces of such heat drawn glass rods are polished and may be coated with a suitable anti-reflection coating. Advantageously, transparent plugs 24, 26 also function in filtering out light in the ultraviolet range to thereby protect light transmissive medium 22 from the damaging effect of the ultraviolet radiation. Accordingly, ultraviolet radiation emitted by light source 100 is filtered by transparent plug 24 with light source connector 14 prior to entrance into light transmissive medium 22.

Transparent plugs 24, 26 preferably each define an outer diameter which is slightly larger than the inner diameter of inner lining 20 to initially form a friction fit between the plugs 24, 26 and the inner lining. In the preferred embodiment, the diameters of transparent plugs are each about 5 mm. The lengths of transparent plug 24, 26 may range from about 10 mm to about 25 mm. In the preferred embodiment the length of the plugs vary depending on the application and the particular method utilized for mounting the plugs to the tube 10. Mounting methods will be discussed in greater detail below.

Figure 3:
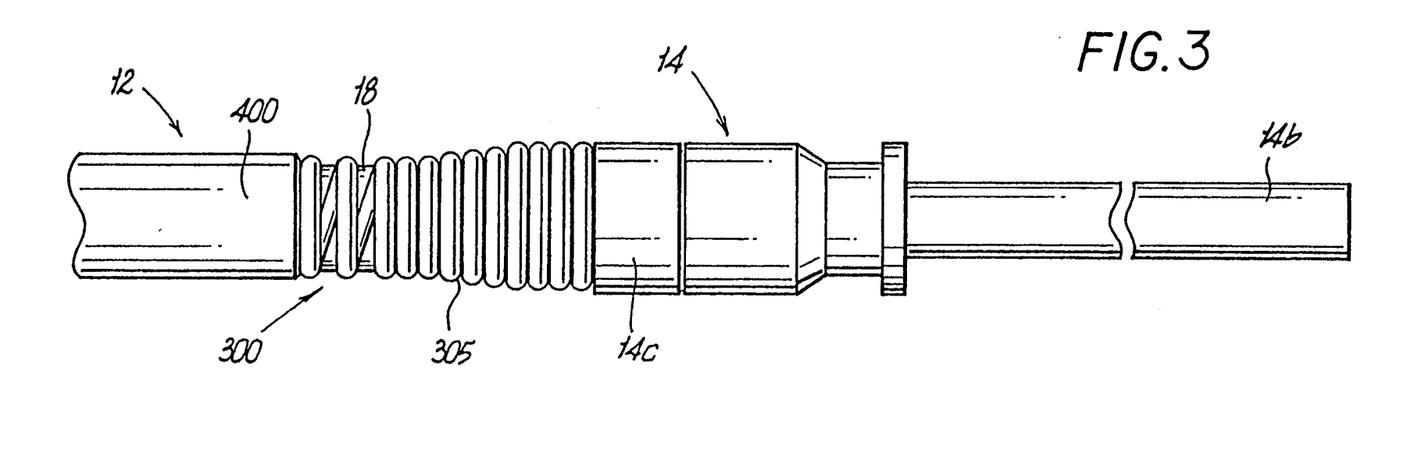
FIG. 3 is an enlarged plan view of the light source connector member of the light guide of FIG. 1.

Referring now to FIGS. 3 and 4, there is illustrated the first or light entry end portion of light guide 10 in detail. In this embodiment of light guide 10, inner lining 20 extends beyond end portion 18a of outer sheath 18 as shown in FIG. 4. Light transmissive end plug 24 is positioned at least partially within inner lining end portion 20a of the liner and is initially retained within the inner lining by a frictional fit formed between plug 24 and the inner lining as previously mentioned. Thereafter, a heat shrinkable tubing 21 is positioned about end plug 24 overlapping end portion 20a of inner lining 20. Heat is applied to tubing 21 to shrink the tubing and attach end plug 24 to inner lining end portion 20a. The shrinkable tubing 21 preferably is made of a material having the same index of refraction as inner liner 20. In the preferred embodiment wherein the inner liner is made of FEP, shrinkable tubing also is made of FEP. Thus, as shown, the overlapping region of the shrink tube and inner lining forms a double layer of FEP tubing surrounding glass plug 24.

End portion 20a of inner liner 20 having end plug 24 secured therein with shrink tubing 21 is then inserted into tube mounting portion 14a of illuminator connector 14 and advanced within the connector 14 until end face 24b of end plug 24 is approximately flush with the open light source inlet end 14b of connector 14 as shown in FIG. 4. End portion 18a of outer sheath 18 is positioned about the periphery of tube mounting portion 14a of connector 14. Thereafter clamp 14c of connector 14 is slid onto mounting portion 14a to securely wedge the outer sheath 18 between the inner crowned surface 23 of clamp 14c clamp and the mounting portion to effect the attachment of the connector to tube 12. Where desired, the portion of connector 14 adjacent glass end plug 24 may be circumferentially crimped or swaged to provided an even more secure connection. This crimping or swaging of the connector is preferably about 2%–4% deformation of the connector over at least a portion of the double layer region of liner 20 and shrink tubing 21. Crimping or swaging in this region not only securely attaches the connector to the tubing, but also securely attaches the shrink tube, inner liner and glass rod without damaging the glass rod. As a further advantage, a tight seal is formed at the crimp by tightly compressing the double layers of tubing against the glass plug.

Figure 5:
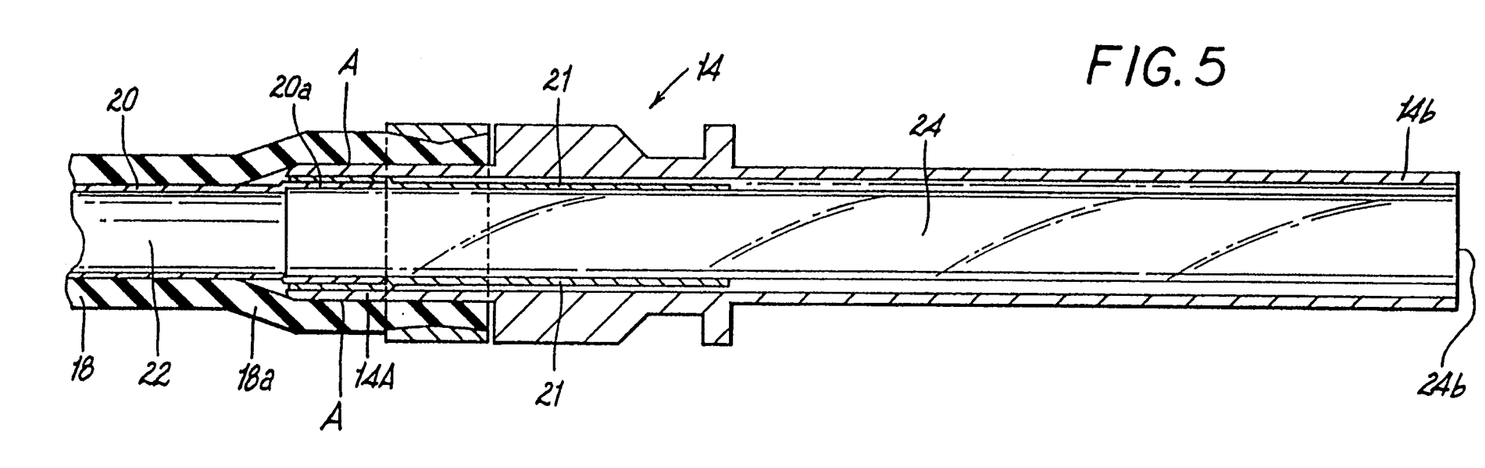
FIG. 5 is an enlarged cross-sectional view of the light source connector of FIG. 3 with an alternative elongated light transmissive end plug positioned therein and illustrating an alternative method for attaching the light source connector member and the elongated end plug to the flexible tube of the light guide.

FIG. 5 illustrates an alternative method for attaching illuminator connector 14 to elongated tube 12. In accordance with this method, transparent end plug 24 is elongated and is approximately the same length as the length of illuminator connector 14, i.e., approximately 80 mm. A portion of end plug 24 is inserted into inner lining end portion 20a. Thereafter, a heat shrinkable tubing 21 is positioned about inner lining end portion 20a and over a substantial portion of end plug 24. Heat is applied to shrink tubing 21 to effect the attachment of inner lining 20 to end plug 24. Thereafter, inner lining end portion 20a with mounted end plug 24 and shrinkable tubing 21 is positioned within tube mounting portion 14a of illuminator connector 14 and advanced within the connector 14 such that end face 24b of plug 24 is adjacent light source mounting portion 14b of connector 14.

At this point, if desired, tube mounting portion 14a may be crimped at position A to retain end plug 24 in the appropriate position within connector 14. As set forth above, preferably, the material of tube mounting portion 14a is crimped slightly, e.g., at about 2%–4% deformation. The attachment of connector 14 is continued by positioning outer sheath portion 18 over mounting portion 14a of connector 14 where clamp 14c is slid to the appropriate position to clamp the sheath to the connector.

FIG. 6 illustrates another alternative method for attaching end plug 24 and illuminator connector 14 to elongated tube 12. This alternative method is similar in most respects to that described above in connection with FIG. 5 except that the inner lining end portion 20a extends along the entire length of end plug 24. Thus, the cladding effect of inner liner 20 is maintained throughout the length of end plug 24. The attachment of end plug 24, shrinkable tubing 21 and illuminator connector 14 is achieved in a similar manner to that described in connection with FIG. 5.

Figure 7:
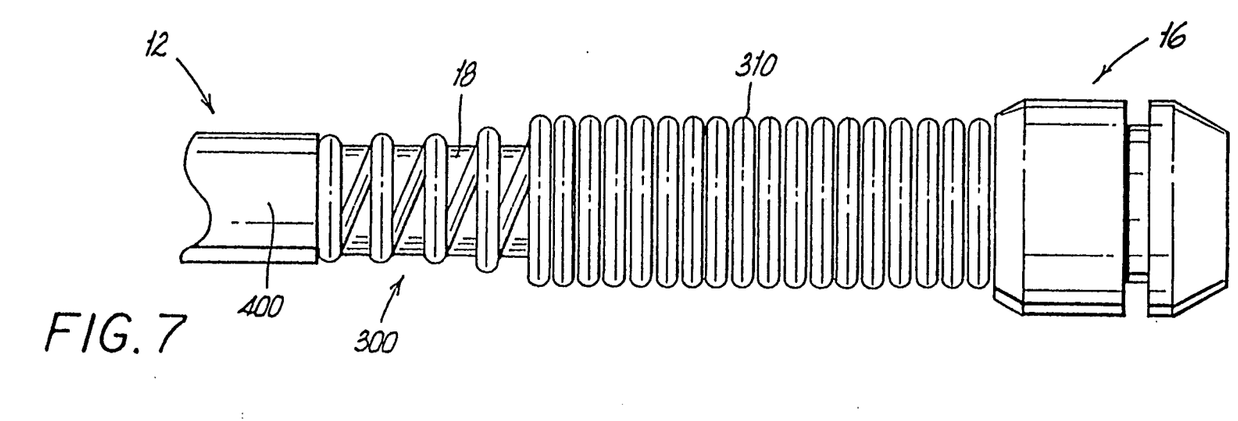
FIG. 7 is an enlarged plan view of the endoscope connector member of the light guide of FIG. 1.
Figure 8:
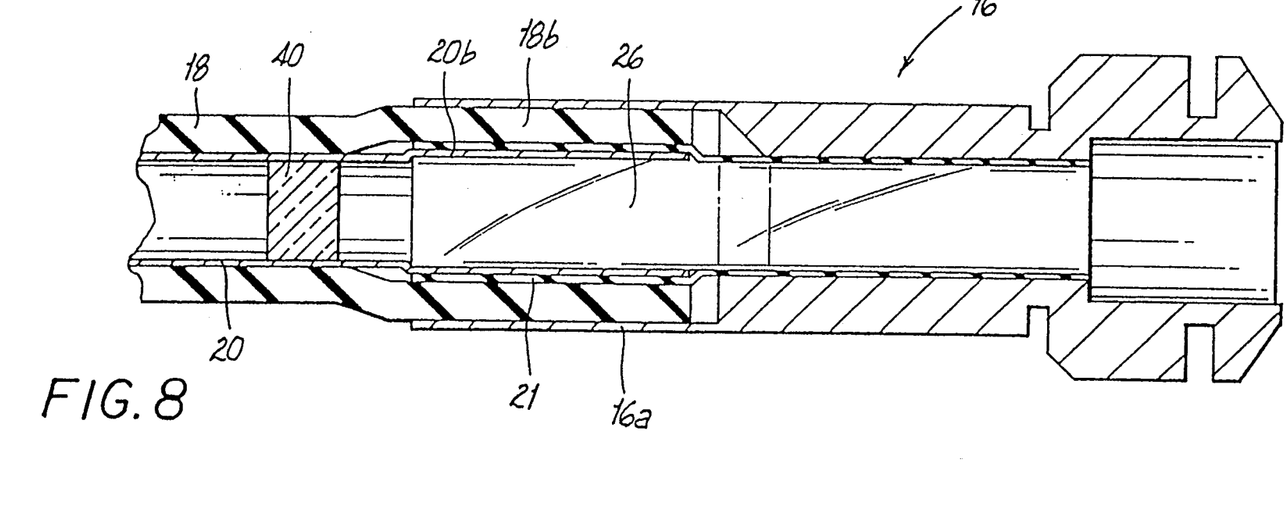
FIG. 8 is an enlarged cross-sectional view of the endoscope connector member of FIG. 7 with a light transmissive end plug positioned therein and illustrating a preferred method for attaching the endoscope connector member and the end plug to the tube of the light guide.

Referring now to FIGS. 7–8, there is illustrated the second or light exit end portion of light guide 10. End plug 26 is positioned at least partially within inner lining end portion 20b and a heat shrinkable tubing 21 is positioned about end plug 26 and overlapping end portion 20b. Heat is applied to tubing 21 to effect the attachment of end plug 26 to inner lining 20. If desired, tube mounting portion 16a may be slightly crimped to facilitate the attachment in a manner similar to that described above. Thereafter sheath end portion 18b is positioned about tubing 21 and inner lining end portion 20b and inserted within tube mounting portion 16a of endoscope connector 16. In the preferred embodiment, the effective outer diameter of sheath end portion 18b having end plug 26 inserted therein approximates the inner diameter of tube mounting portion 16a of connector 10 to form a frictional fit to thereby attach connector 10 to tube 12.

The connectors shown and discussed above are preferred but it will be understood that any other suitable connector member may be substituted therefor.

In FIGS. 1, 3, 7 and 9 the portion of coiled spring member 300 is shown exposed and not covered by shrink tube cover 400. Coiled spring 300 has been shown in this manner as a means of discouraging re-sterilization of the light guide. Thus, by leaving exposed at least a portion of the coil spring it is more difficult to clean the light guide for re-sterilization, which may discourage attempted re-sterilization. The portion of the coil spring adjacent the connectors is shown exposed because that area is handled most during use and is most likely to be contaminated and, hence, to require the most attention during attempted re-sterilization. Of course, it is also contemplated that shrink tube cover 400 could cover the entire coil spring, including the juncture with the connector. Fully covering the coil spring may be desirable to provide further rigidity at the connection of the tubing to the connectors and to further minimize potential light leakage.

In a first method of manufacture of light guide 10, tube 12 is immersed in the degassed mineral oil prepared in the manner described above. The ends of the tube are raised with the liquid filled tube 12 draped in a U-shape. The end portion 12a, 12b are plugged with end plugs 24, 26 respectively. Thereafter, shrinkable tubings are secured about end plugs 24, 26 and connectors 14, 16 are attached in the above-described manner. In an alternative fabrication method, the mineral oil can be drawn into tube 12 under Vacuum.

Referring again to FIG. 1, light guide 10 may have a coiled spring member 300 positioned about the periphery of tube 12. Spring member 300 prevents kinking of tube 12 and serves in providing support to the tube. Preferably, the inner diameter of spring 300 approximates the outer diameter of tube 12. As shown in FIGS. 3 and 7, spring member is expanded to a desired dimension at its end portions 305, 310, and thereafter compressed to fit about the tube mounting portions 14a, 16a of illuminator connector 14 and endoscope connector 16, respectively. Such configuration of spring end portions 305, 310 provides additional support at the junctures of tube 12 and connectors 14, 16. A cover, preferably in the form of a shrinkable tubing 400, may be adjacent connectors 14, 16 positioned inside or outside of spring member 300 to enclose the spring. For added support, particularly shrink tubing may be placed both inside and outside the spring member. Optionally, the spring member 300 is left wholly or partially exposed on an outer surface of the light guide to discourage attempts at resterilization.

Referring still to FIG. 1, light guide 10 is intended to be used with endoscope 200 having endoscope housing 204 and an elongated endoscopic portion 206 extending distally of the housing 204. Examples of endoscopes which can be readily used with light guide 10 are disclosed in U.S. Pat. Nos. 3,089,484; 3,257,902; 4,784,118; 4,964,710 and 5,188,092, the contents of each being incorporated herein by reference. Endoscopic portion 206 incorporates an image transferring system which may include a plurality of fiber optic elements to transfer an image formed at an image plane to eyepiece 208 of the endoscope. Alternatively, a series of optical lens components may be used instead of the fiber optic handle to transfer an image to the viewer. Known relay optical systems include those shown and described in U.S. Pat. Nos. 3,089,484; 3,259,902 and the aforementioned 4,964,710.

Light source 100 may be any known illuminating source including, for example, the Lumatic model Superlite light source, halogen lamps, Argon or He-Ne lasers, tungsten filament incandescent lamps, sources available from Karl Storz, Inc., Richard Wolf etc.

Light guide 10 is highly effective in conveying illuminating light from light source 100 to endoscope 200. Due to the strategic selection of the materials of the liquid transmitting medium 22 (mineral oil), inner lining 20 (FEP) and end plugs 24, 26 (drawn Pyrex or quartz glass rods having substantially the same index of refraction as liquid medium 22), light guide 10 advantageously has a relatively large numerical aperture compared to conventional fiber optic light guides. In particular, the numerical aperture of light guide 10 is approximately 0.63.

Further, the strategic selection of materials makes light guide 10 substantially less expensive to manufacture than conventional fiber optic light guides, so that the light guide efficiently may be disposed of after a single use. Indeed, the light cable in accordance with the invention may be manufactured and sold in an economic manner which might render re-sterilization more costly than disposal.

Figure 9:
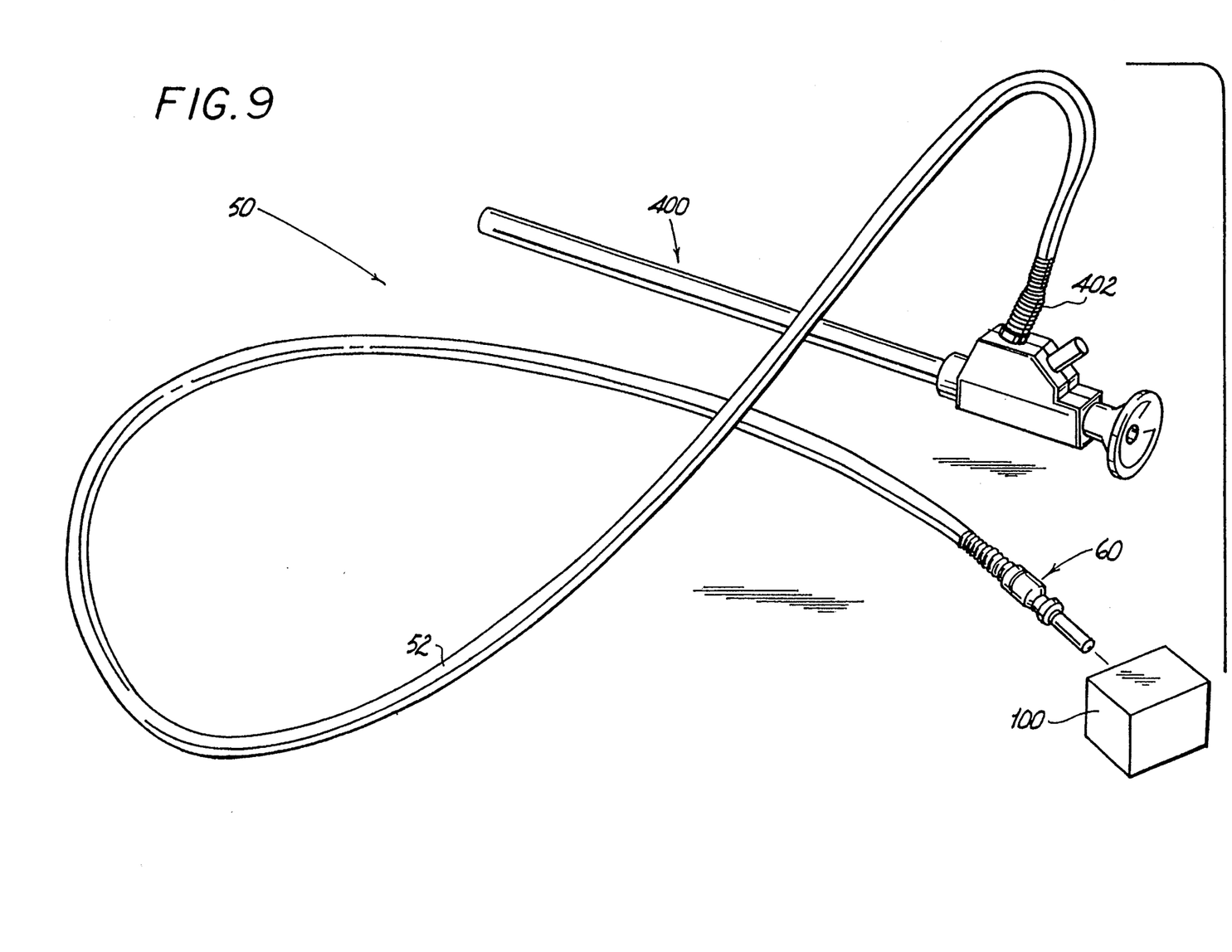
FIG. 9 is a perspective view of a liquid light guide constructed in accordance with another embodiment of the present invention wherein the light guide is integrally formed with the endoscope.

Although in the preferred embodiment of FIG. 1 light guide 10 is a separate component from endoscope 200, it is envisioned that light source 10 may be an integral part of endoscope 200 thus forming a single light guide endoscope unit. Referring to FIG. 9, light guide 50 is integrally connected to endoscope 400. In a first embodiment of light guide 50 the light guide constructed as described above is simply attached by permanent attachment so that the glass plug abuts the endoscope illumination connection. Alternatively, it is contemplated that only one end plug is required to seal flexible tube 52, i.e., at the tube end portion adjacent illuminator connector 60. The other end portion of tube 52 may be directly connected to inlet port 402 of endoscope 400. Thus, the light transmissive fluid within tube 52 directly contacts the proximal end of illumination system within the endoscope, e.g., the ends of the fiber optic bundle, of endoscope 400. Preferably, in this embodiment, endoscope 400 is of the disposable type, thus making it cost effective to dispose of the light guide/endoscope unit together after a single use.

To the extent not already indicated, it also will be understood by those of ordinary skill in the art that any one of the various specific embodiments herein described and illustrated may be further modified to incorporate features shown in other of the specific embodiments.

By way of example, it may be desirable to permanently attach the light cable to an endoscope, such as a disposable endoscope, to assure that the shortcomings of a failing reusable fiber optic light cable are not blamed upon the endoscope. Particularly where a disposable endoscope is being used for the first time, it would be undesirable for the user incorrectly to conclude that the endoscope is of inferior quality when, in fact, any imaging difficulties are associated with a reusable fiber optic light guide of inferior transmission quality.

The invention in its broader aspects therefore is not limited to the specific embodiments herein shown and described but departures may be made therefrom within the scope of the accompanying claims without departing from the principles of the invention and without sacrificing its chief advantages. By way of example only, it will be understood by those skilled in the art that while outer sheath 18, coil spring 300 and shrink tube cover 400 all provide sufficient rigidity to resist kinking and bending during use, numerous variations and combinations may be used to obtain this result. Thus, a foam jacket might be used in place of some or all of the foregoing, or might be used in combination with some or all of them. Similarly, additional stiffening structures, such as multiple layers of shrink tubing, might be provided adjacent the connectors where bending during use is likely to occur. Similarly, if no shrink tube cover is used a certain amount of light leakage will occur through the wall of the tubing. This may be objectionable in a darkened operating room, so it is contemplated that the entire light guide may be covered With an opaque cover such as the shrink tubing described herein. Alternatively, it is contemplated that the tubing used to contain the transmissive medium could be pigmented to reduce light transmission. Thus, in the embodiments described herein the outer sheath could be pigmented to reduce glare.

What is claimed is:

1. A liquid light guide for surgical instrumentation, which comprises:
    a flexible elongated tube having first and second end portions;
    first and second light transmissive members disposed at respective first and second end portions of said elongated tube, to substantially seal an interior portion of said elongated tube; and
    a light transmissive medium filling said interior portion of said elongated tube, said light transmissive medium comprising a heavy mineral oil having a specific gravity greater than or equal to about 0.86.

2. The light guide according to claim 1 wherein said elongated tube comprises an inner tube for containing said light transmissive medium and an outer sheath.

3. The light guide according to claim 2 wherein the index of refraction of the material of said inner tube is less than the index of refraction of said light transmissive medium.

4. The light guide according to claim 3 wherein said inner tube comprises a fluorinated ethylene polymer.

5. The light guide according to claim 3 wherein said inner lining of said elongated tube comprises polytetrafluoroethylene.

6. The light guide according to claim 1 wherein said first and second light transmissive members comprise light transmissive transparent plugs, each said transparent plug dimensioned and configured to be inserted into an end portion of said elongated tube.

7. The light guide according to claim 6 wherein the material of said transparent plugs has an index of refraction substantially equal to the index of refraction of said light transmissive fluid.

8. The light guide according to claim 6 wherein said transparent plugs comprise drawn glass rods.

9. The light guide according to claim 7 wherein each said transparent plug comprises a material selected from the group consisting of quartz, quartz glass and pyrex.

10. The light guide according to claim 8 wherein said glass rods have polished end faces.

11. The light guide according to claim 10 wherein each said polished end face of said glass rods is coated with an anti-reflection coating.

12. The light guide according to claim 1 further comprising means for connecting said first end portion of said elongated tube to a light source.

13. The light guide according to claim 1 further comprising means for connecting said second end portion of said elongated tube to an illumination portion of said surgical instrumentation.

14. The light guide according to claim 1 further comprising a support member disposed about at least a portion of said elongated tube, said support member dimensioned and configured to provide support to said elongated tube.

15. The light guide according to claim 14 wherein said support member comprises a spring member coiled around said elongated tube.

16. The light guide according to claim 15 further comprising a cover member disposed around at least a portion of said spring member.

17. In combination with an endoscope including means for transferring light from a proximal inlet portion to a distal outlet portion, a flexible light guide for supplying illuminating light from an illumination source to said proximal inlet portion of said endoscope, said flexible light guide comprising a flexible tube member having first and second end portions and being filled with a light transmissive fluid, said light transmissive fluid comprising a heavy mineral oil having a specific gravity equal to or greater than 0.86, said flexible tube member being fabricated from a material having an index of refraction less than the index of refraction of said light transmissive fluid, said light guide further including sealing means for sealing at least said first end portion of said flexible sheath member.

18. The combination of claim 17 wherein said sealing means comprises a first transparent light transmissive plug at least partially positioned within said first end portion of said flexible tube member.

19. The combination of claim 18 further comprising an illuminating connector for connecting said first end portion of said flexible tube member to an illuminating source.

20. The combination of claim 18 further comprising an endoscope connector for connecting said second end portion of said flexible tube member to said proximal inlet portion of said endoscope.

21. The combination of claim 18 wherein said sealing means comprises a second transparent light transmissive plug at least partially positioned within said second end portion of said flexible tube member.

22. A method for conveying light from a light source to an endoscope, the endoscope including means for transferring light from a proximal inlet portion to a distal outlet portion to illuminate a body cavity, the method comprising the steps of:

providing a flexible tube member having first and second end portions, first and second light transmissive members disposed at respective first and second ends of said flexible tube member to substantially seal the interior of said flexible tube member and a light transmissive medium filling the interior of said flexible sheath member, said light transmissive member comprising a heavy mineral oil having a specific gravity greater than 0.86;

positioning said first end portion of said flexible tube member adjacent a light source;

positioning said second end portion of said flexible tube member adjacent the proximal inlet portion of the endoscope; and illuminating the light source such that the light emitted by the light source is transmitted through said flexible tube member and out said second end portion where the light is received in the proximal inlet portion of the endoscope and transferred by the transferring means to illuminate the body cavity.

23. The method according to claim 22 wherein said light guide comprises light connecting means attached to said first end portion of said tube member for connecting said first end portion to the light source and wherein said step of positioning said first end portion includes connecting said light connector means to the light source.

24. The method according to claim 23 wherein said light guide comprises endoscope connector means attached to said second end portion of said tube member for connecting said second end portion to the endoscope and wherein said step of positioning said second end portion includes connecting said endoscope connector means to the proximal inlet portion of the endoscope.

25. A disposable liquid light guide comprising:
a flexible plastic elongated tube having first and second end portions;
first and second drawn glass rod members at least partially disposed in respective first and second end portions of said elongated tube to substantially seal an interior portion of said elongated tube;
a light transmissive heavy mineral oil having a specific gravity greater than or equal to about 0.86.

26. The light guide of claim 25 wherein said flexible plastic comprises FEP.

27. The light guide of claim 25 wherein said drawn glass rod members have polished end faces.

28. The light guide of claim 25 wherein said mineral oil is degassed.

29. The light guide of claim 25 further comprising a first connector member attached to said first end portion and a second connector member attached to said second end portion.

30. The light guide of claim 25 wherein said light guide has a numerical aperture of about 0.63.

31. The light guide of claim 25 further comprising a tube member surrounding at least a portion of said glass rod and said respective end portion.

32. The light guide of claim 31 wherein said tube member is a heat shrink tubing.

33. A method of making a liquid light guide comprising the steps of:
   filling a flexible plastic tube with a mineral oil having a specific gravity equal to or greater than about 0.86;
   inserting plug members partially into the ends of said tube;
   placing heat shrink tubing around said plug members overlapping said tube; and
   shrinking said tubing around said plug members.

34. The method of claim 33 further comprising securing connector members to each end of said tubing.

35. The method of claim 33 further comprising securing at least one connector member to one end of said tubing by swaging said connector adjacent said heat shrink tube and said plastic tube.

36. The method of claim 35 further comprising inwardly swaging said connector member in the range of about 2–4%.

37. The method of claim 33 further comprising degassing said mineral oil.

38. The method of claim 37 wherein said step of degassing comprises stirring said mineral oil in a container under vacuum.

* * * * *